United States Patent [19]

Alexander et al.

[11] Patent Number: 4,503,217

[45] Date of Patent: Mar. 5, 1985

[54] PROCESS FOR SELECTIVE PREPARATION OF POLYMERIC POLYAMINES

[75] Inventors: David C. Alexander; John F. Knifton; Susan D. Unvert, all of Austin, Tex.

[73] Assignee: Texaco Inc., White Plains, N.Y.

[21] Appl. No.: 550,346

[22] Filed: Nov. 10, 1983

[51] Int. Cl.³ .............................................. C08G 73/02
[52] U.S. Cl. .................................. 528/392; 525/329.3; 525/332.1; 525/332.9; 525/375; 525/378; 525/379; 525/383; 528/422; 564/467; 564/485; 564/509
[58] Field of Search ................ 528/392, 422; 564/485, 564/467, 509; 525/329.3, 332.1, 332.9, 375, 378, 379, 383

[56] References Cited

U.S. PATENT DOCUMENTS 4,312,965  1/1982  Jachimowicz et al. ............. 528/392

Primary Examiner—Harold D. Anderson
Attorney, Agent, or Firm—Jack H. Park; Kenneth R. Priem; Cynthia L. Kendrick

[57] ABSTRACT

An aminomethylation reaction is disclosed wherein polymeric polyamines are produced. Polymeric polyolefins such as polybutadiene, ammonia, primary or secondary amines, and synthesis gas are reacted in the presence of a catalyst system comprising a ruthenium-containing catalyst, such as triruthenium dodecacarbonyl, and dimethyl formamide as a solvent.

The use of a two-phase solvent mixture consisting of N,N-dimethylformamide plus a hydrocarbon is particularly advantageous in that:

(1) The aminomethylation selectivity is improved and few side reactions results;
(2) The two-phase liquid product mixture obtained, allows easy separation of product polyamine from ruthenium-containing catalyst.

25 Claims, No Drawings

PROCESS FOR SELECTIVE PREPARATION OF POLYMERIC POLYAMINES

FIELD OF THE INVENTION

This invention relates to an aminomethylation process and more particularly this invention relates to the selective preparation of polymeric polyamines from polymeric olefins, amines and synthesis gas in the presence of a catalyst system comprising an appropriate transition metal catalyst, such as a ruthenium-containing compound, for example, in the presence of a single or two-phase solvent system, heating the mixture to a temperature of at least 100° C. and a pressure of at least 100 psi until there is substantial formation of the desired polyamine and separating said polymeric polyamine product by a phase separation technique. The resulting polymeric products are useful as surfactants, surfactant precursors and wet strength agents for paper products.

BACKGROUND OF THE INVENTION

The principle of obtaining amines starting from an olefin, hydrogen, carbon monoxide and a primary or secondary amine is known. Various techniques embodying this principle have been described using catalysts of various kinds.

Early work in this field taught that aliphatic acids may be obtained by reacting carbon monoxide with an olefin and steam and that ammonia may be reacted with carbon monoxide to produce formamide. U.S. Pat. No. 2,422,632 (1944) appears to be the first work to suggest a process by which an olefin may be reacted with carbon monoxide and ammonia or an amine having replaceable hydrogen to form an amide or amine.

U.S. Pat. No. 2,497,310 (1946) defined a process for the synthesis of aliphatic amines which consisted of introducing carbon monoxide, hydrogen, a compound from the group consisting of ammonia and amines having at least one hydrogen attached to amino nitrogen, an unsaturated compound containing a non-benzenoid double bond between carbon atoms, and a catalytic quantity of cobalt metal, into a pressure resistant vessel and heating the resultant mixture within the range of 50°–350° C. under a reaction pressure in excess of 50 atm, whereby a reaction product containing amines is produced and thereafter separated from the reaction product produced.

In Shell International Research Maatschappy B. V. Neth. Appl. 6,405,802 Nov. 30, 1964; corresponding to U.S. Pat. No. 3,234,283 (1966), tertiary amines are obtained in improved yields and at lower pressures than in prior processes by treating CO, hydrogen and a secondary amine with a $C_{10}$–$C_{13}$ olefinic mixture in the presence of a cobalt carbonyl-tri alkylphosphine catalyst.

U.S. Pat. No. 3,513,200 (1970) covers the utilization of Group VIII metal complexes bearing a biphyllic ligand such as a phosphine and, optionally these complexes may contain a metal hydride complexed with CO. There can be added, as an adjuvant, poly(heterocyclo)amines. The reaction is realized at a temperature between 50° and 200° C. and under a pressure ranging from 5 to 300 atmospheres. A significant proportion of aldehydes is obtained and the selectivity to amines is still in this case only very moderate.

In a paper by Iqbal published in Helvetica Chemica Acta, Volume 54, pages 1440 to 1445 (1971), as well as in U.S. Pat. No. 3,947,458 (1976), the catalytic aminomethylation of olefins is described employing a rhodium oxide catalyst, an iron carbonyl catalyst and a mixed rhodium oxide/iron carbonyl catalyst.

U.S. Pat. No. 4,096,150 (1978) discloses a process for the manufacture of tertiary amines wherein an olefin, hydrogen, CO and secondary amine are reacted in the presence of a coordination complex catalyst of a Group VIII metal and a ligand, the donor atom of which is oxygen, nitrogen or sulfur.

In J. Org. Chem. 45 3370 (1980), Laine, et al. describe the results of their studies on the aminomethylation reaction using a variety of Group VIII transition-metal carbonyl catalyst precursors.

U.S. Pat. No. 4,292,242, by Laine, states that the object of its invention is to provide improved methods of aminomethylation which are more selective and lead to fewer unwanted by-products such as alcohols and carboxy amides. A further object mentioned was to provide a more stable mixed carbonyl catalyst, the use of which would result in higher yields of the desired amines. Here the claimed catalyst is a mixed ruthenium carbonyl/iron carbonyl in a suitable solvent. Again, this process leads to a formamide by-product.

In J. Org. Chem., 47, 445 (1982), Jachimowicz, et al. discuss the various approaches which have been used to attempt to devise a one-step, efficient and general conversion of olefins to amines. Among the catalysts used in processes devised by various people have been iron pentacarbonyl, rhodium oxide, ruthenium/iron carbonyl and iridium catalysts. The discussion in this article examines the feasibility of various aminomethylation syntheses.

In the processes discussed above, the selective production of a polymeric tertiary amine is not contemplated.

In U.S. Pat. No. 4,297,481, Jachimowicz discloses a process for forming a polymeric polyamine/amide wherein said amino/amido nitrogens are positioned in the polymer backbone by contacting a monomeric nitrogen compound which has at least two labile hydrogens bonded to the nitrogen atoms therein, a monomeric hydrocarbon compound containing at least two olefinic groups therein, carbon monoxide and water in the presence of a catalytic amount of a rhodium-containing compound. This invention describes the use of ammonia or primary amines. The preparation of polymers with pendant amine and amide groups is described in U.S. Pat. No. 4,312,965. These polymers are prepared from polymeric polyolefins, carbon monoxide, and monomeric nitrogen compounds as described previously. Again, rhodium or a rhodium-containing compound serves as catalyst. Isolation of the product polymer is by precipitation with water from an organic solvent.

In prior processes in the art by which aminomethylation takes place, the reaction must often take place at high temperatures and/or pressures, the olefin conversion and selectivity to the desired tertiary amines is not as high as desired, and unwanted by-products are often formed. Additionally separation of the product polymer is by means such as precipitation which do not allow easy catalyst recycle.

It would be a considerable advance in the art to devise a system for selectively producing tertiary polymeric amines from CO, hydrogen, polymeric olefins and secondary amines by an aminomethylation process which results in a product with a high percentage of polymeric tertiary amines. The resulting polymeric amines are useful as surfactants, wet strength agents and flocculating agents. In such applications the polymeric products are desirable and, as stated, it would be a considerable advance to provide them in substantial yield. In addition, it would be an advance over prior art to devise a process with good selectivity which proceeds under mild reaction conditions, without undesired side reactions and affords easy and efficient separation of the desired product, free of catalyst.

SUMMARY OF THE INVENTION

These and other desirable results are achieved by the process of this invention comprising preparing polymeric polyamines by an aminomethylation process which comprises reacting a polymeric polyolefin, ammonia, primary or secondary amine, and synthesis gas (a mixture of carbon monoxide and hydrogen) in the presence of a ruthenium-containing catalyst system and a single or two-phase solvent medium, and heating the resulting mixture to a temperature of at least 100° C. and a pressure of at least 100 psi until there is substantial formation of the desired polymeric polyamine.

In the presence of certain added solvent media, the desired polymeric polyamine product is separated from said transition metal catalyst by a phase separation technique, the efficiency of which is determined by the particular choice of solvents.

DETAILED DESCRIPTION OF THE INVENTION

In the broadest aspect of this invention polymeric polyamines are prepared from a polymeric polyolefin, synthesis gas (a mixture of carbon monoxide and hydrogen), and ammonia or a primary or secondary amine in the presence of a catalyst system comprising compounds of ruthenium and a single or two-component solvent medium and heating the resultant mixture to a temperature of at least 100° C. and a pressure of at least 100 psi until there is substantial formation of the desired polymeric polyamine and separating said polymeric polyamine products by a phase separation technique, wherein the solvent allows for easy separation of product from catalyst.

Aminomethylation reactions used in this invention to prepare polymeric polyamines from polymeric polyolefins, synthesis gas (CO/H$_2$) and ammonia or primary or secondary amines can be represented by the following general equation:

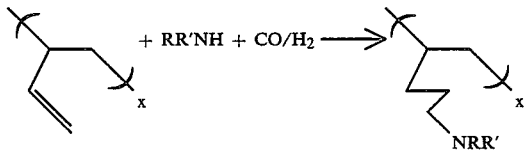

Here, x represents an integer between 2 and 5000 and R and R' may each be hydrogen or hydrocarbyl radicals containing 1 to 20 carbon atoms.

In the process of this invention the ruthenium-containing catalyst is most advantageously used in conjunction with a two-phase liquid solvent media. This two-phase solvent media offers distinct advantages over single phase solvent systems, including improved selectivity to desired polyamine product, fewer side reactions and easier separation of product from catalyst.

In order to present the inventive concept in the greatest possible detail as to promote its understanding, the following supplementary disclosure is submitted.

A. CATALYST COMPOSITION

The group of catalysts suitable in the practice of this invention all contain ruthenium. The actual catalytically active species are unknown, but are believed to comprise ruthenium in complex combination with carbon monoxide and hydrogen.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or ruthenium carbonyl hydride derivative. Here, suitable examples include triruthenium dodecacarbonyl and other ruthenium carbonyl hydrides such as H$_2$Ru$_4$(CO)$_{13}$ and H$_4$Ru$_4$(CO)$_{12}$, and substituted carbonyl species such as the tricarbonylruthenium(II) chloride dimer, [Ru(CO)$_3$Cl$_2$]$_2$.

Preferred ruthenium-containing compounds include oxides of ruthenium, ruthenium salts of an organic carboxylic acid and ruthenium carbonyl or ruthenium carbonyl hydrides derivatives. Among these, particularly preferred as ruthenium(IV) dioxide hydrate, ruthenium tetraoxide, anhydrous ruthenium(IV) oxide, ruthenium acetate, ruthenium(III) acetylacetonate, and triruthenium dodecacarbonyl.

Especially good results were observed with triruthenium dodecacarbonyl.

B. FEEDSTOCK

The feedstock used in the practice of this invention comprises a polymeric olefin, ammonia or primary or secondary amine, carbon monoxide and hydrogen.

The process can be applied to any polymeric polyolefin, including monosubstituted, disubstituted and trisubstituted polymeric polyolefins containing 4 to 20 carbon atoms per monomer, as well as mixtures of the same. The process is particularly suited to the aminomethylation of olefins containing 4 to 8 carbon atoms per monomer. Examples of suitable olefins include polyolefins such as polybutadiene, acrylonitrile-butadiene copolymer and polyisoprene.

Particularly preferred in the practice of this invention is the use of polymers with pendant vinyl groups such as those containing 1,2-polybutadiene units.

Suitable nitrogen-containing coreactants useful in the practice of this invention include ammonia, primary and secondary amines and polyamines containing one to 40 carbon atoms. These amines may be straight or branched chain aliphatic series, they may be cycloaliphatic amines, or they may be aromatic amines. Secondary aliphatic amines which are satisfactory coreactants include dimethylamine, diethylamine, methylethylamine, di(n-propyl)amine, di(iso-propyl)amine, di(ethylhexyl)amine, piperidine, morpholine, di(n-heptyl)a- mine, and di(n-decyl)amine, as well as 2-aminooctane, N-methylaniline and pyrrolidine. Primary aliphatic amines which are suitable coreactants include methylamine, ethylamine, n-propylamine, isobutylamine, n-octylamine, and n-dodecylamine. Aliphatic diamines such as piperazine are also useful in the practice of this invention. Very good results were obtained in the process of this invention using dimethylamine.

The quantity of nitrogen-containing coreactant employed in the instant invention is not critical and may vary over a wide range. In general, however, it is desirable to conduct these syntheses in the presence of sufficient secondary amine so as to satisfy the stoichiometry of equation (1).

C. GAS

The relative amounts of carbon monoxide and hydrogen which can be initially present in the synthesis gas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may, or may not undergo reaction under carbon monoxide hydrogenation conditions, such as carbon dioxide, and hydrocarbons, such as methane, ethane, propane and the like.

D. SOLVENT

The synthesis of polymeric polyamines is optionally achieved in the presence of added solvents. These solvents may comprise a single-phase system, or a two-phase solvent media. For ease of product separation, catalyst separation and improved selectivity to desired polyamine, a two-phase solvent media may be preferred in many cases.

Where the aminomethylation reaction is conducted in a suitable mixture of two largely immiscible solvents (i.e. using a two-phase solvent system), one component need be a polar liquid and the other component, a nonpolar liquid under the conditions of reaction.

Suitable polar solvent components for the practice of this invention may be selected from the group that includes certain carboxylic amides, and certain ethereal solvents.

These solvents should be liquids under the conditions of aminomethylation reaction (eq. 1) and should substantially solubilize the ruthenium-catalyst component.

Suitable amide solvents may be selected from the group of amides that includes N,N-dimethylformamide, N,N-dimethylacetamide, hydroxy-ethylpyrrolidone, N-methylpyrrolidone, N-isopropylpyrrolidone, N,N-diethylformamide, N,N-dimethylacetamide, N,N-dimethylbenzamide, N,N-diphenylformamide, N,N-dimethylbutyramide and N-benzylpyrrolidone.

Examples of suitable ether solvents include p-dioxane, tetrahydrofuran, 2-methoxyethanol, diisopropylether, diphenyl ether, ethyleneglycol dimethyl ether, diethyleneglycol dimethyl ether and triethylene glycol dimethyl ether as well as mixtures thereof.

The second-phase of this two-component solvent mixture is a non-polar liquid selected from the group consisting of aliphatic and aromatic hydrocarbons. Suitable hydrocarbon solvents include octane, n-hexane, mixed hexanes, cyclohexane, petroleum ether fractions, n-decane, benzene, toluene, substituted aromatics as well as mixture thereof.

A preferred class of two-phase solvent components for aminomethylation includes: N,N-dimethylformamide+mixed hexanes, N-N-dimethylformamide+petroleum ether, 2-methoxyethanol+mixed hexanes, and N,N-dimethylformamide+cyclohexane.

Some of the particular advantages noted when adding a N,N-dimethylformamide+n-hexane two-phase solvent to the reaction mixture include:

1. The conversion and selectivity to polymeric polyamines are both higher than in the absence of that solvent, as will be demonstrated by Examples X and XII in comparison to Examples I through IX.
2. The liquid product cleanly separates into two phases, the upper layer of which is rich in polyamine product; the lower layer comprises amide, unreacted amine, plus soluble transition metal catalyst. These layers are easily separated. The lower layer, rich in catalyst, may be recycled.

The amount of solvent employed may vary as desired. In general, it is desirable to use sufficient solvent to fluidize the catalyst system.

Alternatively, the aminomethylation reaction yielding polymeric polyamines may also be usefully conducted using a single-phase solvent media. Here suitable single-phase solvent media include aromatic hydrocarbons. Example X and XII illustrate this case with toluene as the single solvent.

E. CONCENTRATION

The quantity of transition metal compound, such as a ruthenium-containing compound and solvent employed in the instant invention is not critical and may vary over a wide range. In general, the novel process is desirably conducted in the presence of a catalytically effective quantity of active transition metal species and of the solvents which gives the desired product in reasonable yield. The reaction proceeds when employing as little as about $1 \times 10^{-6}$ weight percent and even lesser amounts of, for example, triruthenium dodecacarbonyl.

The upper concentration is dictated by a variety of factors including catalyst cost, partial pressure of carbon monoxide and hydrogen, operating temperature, etc. A ruthenium concentration of from about 0.0001 to about 1 weight percent in conjunction with an amide solvent concentration of from about 10 to about 90 weight percent, based on the total weight of the reaction mixture is desirable in the practice of this invention. The preferred ruthenium to solvent catalyst atomic ratio is from about 0.001 to about 0.010. Generally, in the catalyst system, the molar ratio of the preferred ruthenium compound to the amide solvent will range from about 0.001 to about 0.010. The especially preferred molar ratio is about 1:275.

F. TEMPERATURE

The temperature range which can usefully be employed in the process of the invention may vary over a considerable range depending upon experimental facts, including choice of catalyst, pressure and other variables. The process can take place at from 100° C. to about 300° C. or more. The preferred temperatures are above 120° C. and more preferably between 120° C. and 220° C. Coming under special consideration are temperatures ranging from 150° C. to 190° C.

G. PRESSURE

Superatmospheric pressures of about 100 psi or greater lead to substantial yields of the desired amines. A preferred range is from about 400 psi to about 4000 psi; although pressures above 4000 psi also provide useful yields of the desired products. A preferred range is from 500 psi to about 2000 psi.

The pressures referred to herein represent the total pressure generated by all the reactants although they are substantially due to the carbon monoxide and hydrogen reactants.

H. BY-PRODUCTS

The desired products of the reaction, the polymeric polyamines, are formed in significant quantities with up to 55% of the double bonds undergoing aminomethylation. The desired polymeric products cannot be recovered from the reaction mixture by conventional means such as fractional vacuum distillation, etc., because of their high molecular weights.

This invention demonstrates that transition metal compounds dispersed in solvents, which are active catalysts in, for example, carbonylation reactions, can be used in an aminomethylation reaction to allow for easy and efficient isolation of the product because it is simply a matter of separating the catalyst/polar solvent phase from the polymeric amine/hydrocarbon solvent phase.

In the process of this invention it has been discovered that a two-component mixture solvent, preferably an amide such as N,N-dimethylformamide and a hydrocarbon such as n-hexane as the second solvent component, can be added to the reaction mixture of the aminomethylation reaction to increase rate of reaction, polymeric olefin conversion and selectivity to the desired products. This side reaction of olefin hydrogenation is virtually eliminated.

I. INTRODUCTION OF CATALYST

The process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired polymeric polyamines and said material can be recovered by phase separation. A fraction rich in the catalyst components may then be recycled to the reaction zone, if desired, and additional polymeric polyamine product generated.

IDENTIFICATION TECHNIQUES

The products have been identified in this work by one or more of the following analytical procedures; viz, infrared (ir) spectrophotometry, nuclear magnetic resonance (nmr) and elemental analyses, or a combination of these techniques. All temperatures are in degree centigrade and all pressures in pounds per square inch (psi).

Yields of polymeric tertiary polyamine products have been estimated in accordance with equation (1), basis the quantity of polymeric polyolefin converted, and expressed as a percentile.

To illustrate the process of the invention, the following examples are given. It is to be understood, however, that the examples are given in the way of illustration and are not to be regarded as limiting the invention in any way.

EXAMPLE I

Example I illustrates a typical reaction using the process of this invention. A mixture of polybutadiene with 70% vinylic groupings and 2000 M.N. (7 g, 130 meq unsaturation), diethylamine (12 ml, 117 mmol), mixed hexanes (25 ml), N,N-dimethylformamide (10 ml), and triruthenium dodecacarbonyl (0.1g, 0.16 mmol) was added to a 300 ml stirred stainless steel autoclave which was sealed and purged with $CO/H_2$ (1/1) (by two pressurization/depressurization cycles (200 psi). The reactor was then pressurized to 500 psi with 1/1 $CO/H_2$ and heated to 160° C. Stirring at this temperature was continued for 5 hours.

The product mixture consisted of 2 layers, a lower, clear, dark-red layer (7.4 g) and an upper, clear, light yellow layer (28.5 g).

The upper layer was separated and concentrated under vacuum to give 7 g of a slightly turbid, light yellow viscous product polymer liquid. This material is essentially insoluble in neutral water but soluble in dilute HCl solution or chloroform. By nmr the product polymer is found to contain 27% aminomethylated double bonds and 73% unreacted double bonds.

The nmr spectrum of the lower layer indicated that no more than a trace of polybutadiene was present.

The ruthenium content of the upper layer was 97 ppm and that of the lower layer was 5670 ppm. Ruthenium recovery in the lower layer was estimated therefore to be 90 wt%.

EXAMPLE II-X

Following the procedures of Example I, the experiments of Example II-X, summarized here in Table I, illustrate the aminomethylation of polybutadienes using a ruthenium catalyst precursor and a N,N-dimethylformamide/mixed hexanes two-phase solvent media. It may be noted from an inspection of the data in Table I that:

(a) A variety of polybutadienes of different 1,2-vinyl contents and different molecular weight ranges may be effectively aminomethylated by this technique.
(b) Both ruthenium(IV) oxide and triruthenium dodecacarbonyl are effective ruthenium catalyst precursors.
(c) A number of primary and secondary amines are effective coreactants for the synthesis of polymeric polyamines.
(d) Generally higher degrees of aminomethylation are achieved when the polybutadiene feedstock was a higher vinyl content.
(e) An acrylonitrile-butadiene copolymer may also be effectively aminomethylated by this procedure.

TABLE I[a]

| Example | g pbd | polybutadiene[b] % 1,2 | M.N. | g amine | amine | gas | db/Ru[c] | solv. | g prod | aminated, % | product polymer unreacted, % | reduced, % | Ru, ppm[d] poly/low |
|---|---|---|---|---|---|---|---|---|---|---|---|---|---|
| II | 18.0 | 20 | | 25.6 | Et$_2$NH | 1/1 | 160 | 35/75 | 13 | 22 | 78 | <1 | |

TABLE I-continued

| Example | g pbd | polybutadiene[b] % 1,2 | M.N. | g amine | amine | gas | db/Ru[c] | solv. | g prod | aminated, % | product polymer unreacted, % | reduced, % | Ru, ppm[d] poly/low |
|---|---|---|---|---|---|---|---|---|---|---|---|---|---|
| III | 24.0 | 45 | 4500 | 35.5 | Et$_2$NH | 1/1 | 170 | 50/50 | 20 | 27 | 73 | <1 | |
| IV | 110 | 45 | 4500 | 130 | Me$_2$NH | 1/1 | 130 | 500/500 | 110 | 33 | 67 | <1 | |
| V | 20.0 | 45 | 4500 | 24.8 | Et$_2$NH | 1/1 | 160 | 20/50 | 14 | 29 | 70 | <1 | 156/7220 |
| VI | 7.0 | 70 | 2000 | 8.5 | Et$_2$NH | 1/2 | 280 | 10/25 | 11 | 39 | 61 | <1 | 27/5640 |
| VII | 7.0 | 70 | 1000 | 8.5 | Et$_2$NH | 1/2 | 280 | 10/25 | 10 | 29 | 71 | <1 | 12/4920 |
| VIII | 7.0 | 70 | 2000 | 8.5 | pyrr. | 1/2 | 280 | 10/25 | 6.0 | 33 | 67 | <1 | |
| IX | 9.7 | 70 | 1000 | 8.0 | PrNH$_2$ | 1/2 | 385 | 10/25 | 5.5 | 49 | 51 | <1 | |
| X[e] | 3.0 | | | 7.1 | Et$_2$NH | 1/1 | 58 | 15/25 | 6.0 | 24 | 76 | <1 | |

[a]In all reactions except Examples II and IV Ru$_3$(CO)$_{12}$ was the Ru source; in these RuO$_2$ hydrate was used. Numbers in the solv. column specify ml of polar and nonpolar solvents used. In Examples II and IV petroleum ether (b.p. 35-60° C.) and cyclohexane, respectively, were used as nonpolar solvent. In all other reactions isomeric hexanes were the nonpolar solvent. In all cases dimethyl formamide was the polar solvent. Gas refers to the ratio CO/H$_2$. Pyrr. is pyrrolidine. Reactions were run for 4-5 hrs. at 160° C. and 500-700 psi. In Examples III-IX tetrabutylphosphonium bromide was present (P/Ru = 3-7); this was found to have little or no effect on the course of the reaction.
[b]% 1,2 refers to the vinyl content of the polybutadiene; M.N. is the number average molecular weight, where available; g pbd is the amount of polybutadiene used.
[c]db/Ru is the meq. unsaturation in the polymer/mg-atoms Ru charged.
[d]Ruthenium contents of polymer (1 g/5 ml) hexane) and lower layer from the reaction.
[e]The polymeric reactant was an acrylonitrile-butadiene copolymer.

EXAMPLES XI-XIII

Following the procedures of Example I, the experiments of Example XI-XIII, summarized here in Table II, illustrate the aminomethylation of polybutadienes using toluene alone, and a 2-methoxy ethanol/hexanes as a two-phase solvent mixture. Generally inferior results are obtained with these solvent combinations in comparision with the data in Table I; although the desired aminomethylation does occur, saturation of the polyolefin also takes place to some degree.

TABLE II[a]

| Example | g pbd | polybutadiene[b] % 1,2 | M.N. | g amine | amine | gas | db/Ru | solv. | g prod | aminated, % | product polymer unreacted, % | reduced, % |
|---|---|---|---|---|---|---|---|---|---|---|---|---|
| XI[b] | 7.0 | 45 | 4500 | 8.5 | Et$_2$NH | 1/2 | 130 | 50 | 3.5 | 17 | 39 | 43 |
| XII[c] | 5.0 | 70 | 2000 | 6.4 | Et$_2$NH | 1/2 | 195 | 7/18 | 4.5 | 26 | 59 | 15 |
| XIII[b] | 4.0 | 20 | | 8.5 | Et$_2$NH | 1/2 | 130 | 50 | 4.0 | 8 | 69 | 22 |

[a]Conditions as described in Table I.
[b]Solvent was toluene.
[c]Solvent mixture was N—methoxyethanol/hexanes.

EXAMPLE XIV-XV

Examples XIV and XV demonstrate that the ruthenium-containing catalyst (lower) layer from these aminomethylation reactions of Example I-IX can be easily recycled.

After separation of the layers resulting from the reaction of Example XIV, the lower layer was recharged to the autoclave along with a fresh solution of polybutadiene in hexanes. The reaction was then carried out and worked up as before. It can be seen that very little loss of amination activity occurs and product quality (in terms of degree of aminomethylation versus reduction) is maintained during this catalyst recycle run.

vinylic, M.W.=1000), 0.1 g (0.16 mmol) Ru$_3$(CO)$_{12}$, and 10 ml each of hexanes and N-methylpyrrolidinone was charged to a 300 ml stirred stainless steel autoclave which was sealed and flushed with CO/H$_2$ (1/2). Ammonia (6.0 g, 353 mmol) was added and the mixture was pressurized to 400 psi with CO/H$_2$ (1/2). The reaction was then heated to 180° C., with CO/H$_2$ added at 130° C. to increase the pressure from 495 psi to 650 psi. The reaction time was 5 hours and the final pressure was 640 psi. The product obtained in this case consisted of a red liquid (4 g) and a light brown, rubbery polymeric solid, insoluble in aq. HCl and chloroform, which weighed 6.8 g after being heated at 100°-110° in vacuo for 4 hours. The insolubility of this material precluded nmr analysis, but nitrogen analysis showed 1.92% nitrogen incorporation into this polymer.

What is claimed is:

1. A process for selectively preparing polymeric polamine which comprises reacting a mixture comprising a polymeric poly-olefin reactant, a nitrogen-containing compound reactant, carbon monoxide reactant, hydrogen reactant and a catalyst system comprising a ruthenium-containing compound, and a single or two-phase solvent, at a temperature of at least 100° C. and a pressure of at least 100 psi until there is substantial for- TABLE III[a]

| Example | g pbd | polybutadiene[b] % 1,2 | M.N. | g amine | amine | gas | db/Ru[c] | solv. | g prod | aminated, % | product polymer unreacted, % | reduced, % | Ru, ppm[d] poly/low |
|---|---|---|---|---|---|---|---|---|---|---|---|---|---|
| XIV | 7.0 | 70 | 1000 | 8.5 | Et$_2$NH | 1/2 | 280 | 10/25 | 7.0 | 29 | 71 | <1 | |
| XV | 7.0 | 70 | 2000 | 8.5 | Et$_2$NH | 1/2 | 280 | 10/25 | 8.0 | 26 | 73 | <1 | 128/4570 |

[a]Conditions as described in Table I.

EXAMPLE XVI

In Example XVI ammonia serves as amine coreactant. A mixture of 6.0 g (111 meq) polybutadiene (70% mation of the desired polymeric polyamine and separating the resulting polyamine.

2. The process of claim 1 wherein the polyamine has repeating units containing 4 to 20 carbon atoms.

3. The process of claim 1 wherein the polymeric poly-olefin is selected from the group consisting of polybutadiene, butadiene styrene copolymer and acrylonitrile-butadiene polymer.

4. The process of claim 1 wherein the polymeric olefin is polybutadiene containing 1,2-polybutadiene,

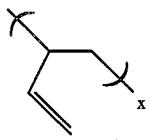

wherein x is an integer of from 2 to 5000.

5. The process of claim 1 wherein the nitrogen-containing compound is selected from the group consisting of ammonia, primary amines and secondary amines.

6. The process of claim 5 wherein the secondary amine is selected from the group consisting of pyrrolidine, diethylamine, dimethylamine, morpholine and di-n-propyl-amine.

7. The process of claim 5 wherein the primary amine is selected from the group consisting of methylamine, ethylamine, n-propylamine, and tert-butylamine.

8. The process of claim 1 wherein the process is conducted with a ratio of CO to $H_2$ of about 1:5 to 5:1.

9. The process of claim 1 wherein the ruthenium-containing compound is selected from the group consisting of oxides of ruthenium, ruthenium salts of a mineral acid, ruthenium salts of an organic carboxylic acid, ruthenium complexes with carbonyl-containing ligands, ruthenium carbonyls and ruthenium carbonyl hydrides and substituted carbonyl species.

10. The process of claim 1 wherein the ruthenium-containing compound is selected from the group consisting of ruthenium dioxide hydrate, ruthenium tetraoxide, anhydrous ruthenium(IV) oxide, ruthenium acetate, ruthenium(III) acetylacetonate and triruthenium dodecacarbonyl.

11. The process of claim 10 wherein the ruthenium-containing compound is selected from the group consisting of ruthenium(IV) oxide and triruthenium dodecacarbonyl.

12. The process of claim 1 wherein the two-phase solvent media consists of a non-polar solvent component and a polar solvent compound.

13. The process of claim 12 wherein the non-polar solvent component is selected from the group consisting of aliphatic and aromatic hydrocarbons.

14. The process of claim 12 wherein the polar solvent component is selected from the group consisting of carboxylic amides and ethereal solvents.

15. The process of claim 12 wherein the aliphatic and aromatic hydrocarbons are selected from the group consisting of n-hexane, octane, petroleum ether fractions, mixed hexanes, benzene, cyclohexane, toluene and substituted aromatics.

16. The process of claim 14 wherein the carboxylic amide are selected from the group consisting of N,N-dimethylformamide, N,N'-dimethylacetamide and N-methylpyrrolidone.

17. The process of claim 14 wherein the ethereal solvent is selected from the group consisting of p-dioxane, 2-methoxyethanol and triethyleneglycol dimethyl ether.

18. The process of claim 1 wherein the single-phase solvent media is an aromatic hydrocarbon.

19. The process of claim 18 wherein the aromatic solvent is toluene.

20. The process of claim 12 wherein the two-phase solvent media consists of N,N-dimethylformamide plus mixed hexanes.

21. The process of claim 1 wherein the temperature range is from 100° to 300° C.

22. The process of claim 25 wherein the temperature range is from 120° C. to 220° C.

23. The process of claim 1 wherein the pressure is from 400 psi to 4000 psi.

24. The process of claim 27 wherein the pressure is from 500 psi to 2000 psi.

25. A process for preparing a polymeric polyamine which comprises reacting a mixture comprising a polymeric polyolefin reactant, a nitrogen-containing compound reactant, carbon monoxide reactant, hydrogen reactant, a catalyst system comprising a ruthenium-containing compound, and a solvent mixture consisting of amide and aliphatic hydrocarbon, at a temperature of at least 120° C. and a pressure of at least 500 psi until there is substantial formation of the desired polymeric polyamine, separating reaction mixture into two distinct phases consisting of an upper phase containing polymeric polyamine, and a lower phase containing reusable catalyst, by-products and other substances, removing the upper phase and recovering desired polymeric polyamine.

* * * * *